(12) United States Patent
Hartley et al.

(10) Patent No.: US 7,753,918 B2
(45) Date of Patent: *Jul. 13, 2010

(54) MEDICAL GRASPING DEVICE

(75) Inventors: David Ernest Hartley, Subiaco (AU);
Krasnodar Ivancev, Lund (SE);
Werner D. Ducke, Greenwood (AU);
Michael P. DeBruyne, Bloomington, IN
(US); Jarett Diamond, Bloomington, IN
(US); Mark R. Frye, Bloomington, IN
(US)

(73) Assignees: William A. Cook Australia Pty. Ltd.,
Brisbane, Queensland (AU); **Cook
Incorporated**, Bloomington, IN (US);
William Cook Europe ApS,
Bjaeverskov (DK)

( * ) Notice: Subject to any disclaimer, the term of this patent is extended or adjusted under 35 U.S.C. 154(b) by 719 days.

This patent is subject to a terminal disclaimer.

(21) Appl. No.: 11/725,944

(22) Filed: Mar. 20, 2007

(65) Prior Publication Data
US 2007/0239141 A1    Oct. 11, 2007

Related U.S. Application Data

(63) Continuation-in-part of application No. 10/828,094, filed on Apr. 20, 2004, and a continuation-in-part of application No. 10/814,018, filed on Mar. 31, 2004, and a continuation-in-part of application No. 10/814,989, filed on Mar. 31, 2004, and a continuation-in-part of application No. 10/003,011, filed on Nov. 1, 2001.

(60) Provisional application No. 60/784,126, filed on Mar. 20, 2006, provisional application No. 60/245,811, filed on Nov. 3, 2000.

(51) Int. Cl.
*A61B 17/08* (2006.01)

(52) U.S. Cl. ..................................................... 606/108
(58) Field of Classification Search ................. 606/200, 606/113, 108, 1, 114, 127, 207, 159, 170
See application file for complete search history.

(56) References Cited

U.S. PATENT DOCUMENTS 2,087,108  A    7/1937  Irvine (Continued)

OTHER PUBLICATIONS

International Search Report Issued on PCT/US07/006890, Oct. 4, 2007.

(Continued)

*Primary Examiner*—Pedro Philogene
(74) *Attorney, Agent, or Firm*—Richard J. Godlewski

(57) ABSTRACT

A medical grasping device (1) has an elongate control member (9) with a grasping member (17) proximal to its distal tip. An outer sheath (3) with a passageway therethrough surrounds the elongate control member and is relatively movable with respect to the control member. A control assembly (2) disposed at a proximal end of said outer sheath has a fixed handle (5) and a sliding handle (7) and the proximal end of the elongate control member is fixed to the sliding handle to move the control member. The grasping member (17) has a plurality of pre-formed wire loops (50, 52, 54, 56) which self-deploy transversely upon emerging from said distal end of said outer sheath. Each wire loop is fastened to substantially opposite sides of the elongate control member so that each of said wire loops is substantially semi-circular upon full deployment and the respective ends (27, 29) of each wire loop extend substantially in opposite directions from the elongate control member.

22 Claims, 8 Drawing Sheets

U.S. PATENT DOCUMENTS

| | | | |
|---|---|---|---|
| 4,727,873 | A | 3/1988 | Mobin-Uddin |
| 5,098,440 | A | 3/1992 | Hillstead |
| 5,133,733 | A | 7/1992 | Rasmussen et al. |
| 5,324,306 | A | 6/1994 | Makower et al. |
| 5,464,408 | A | 11/1995 | Duc |
| 5,779,680 | A | 7/1998 | Yoon |
| 5,782,839 | A | 7/1998 | Hart et al. |
| 5,873,876 | A | 2/1999 | Christy |
| 5,974,978 | A | 11/1999 | Brown et al. |
| 6,036,717 | A | 3/2000 | Mers Kelly et al. |
| 6,162,209 | A | 12/2000 | Gobron et al. |
| 6,187,017 | B1 | 2/2001 | Gregory, Jr. |
| 6,221,048 | B1 | 4/2001 | Phelps |
| 6,241,738 | B1 | 6/2001 | Dereume |
| 6,280,464 | B1 | 8/2001 | Hayashi |
| 6,348,056 | B1 | 2/2002 | Bates et al. |
| 6,364,887 | B1 | 4/2002 | Dworschak et al. |
| 6,458,139 | B1 | 10/2002 | Palmer et al. |
| 6,458,145 | B1 | 10/2002 | Ravenscroft et al. |
| 6,468,291 | B2 * | 10/2002 | Bates et al. ............ 606/200 |
| 6,589,231 | B1 | 7/2003 | Gobron et al. |
| 6,755,847 | B2 | 6/2004 | Eskuri |
| 6,837,901 | B2 | 1/2005 | Rabkin et al. |
| 6,893,451 | B2 | 5/2005 | Cano et al. |
| 6,939,370 | B2 | 9/2005 | Hartley et al. |
| 7,101,379 | B2 | 9/2006 | Gregory, Jr et al. |
| 7,344,550 | B2 * | 3/2008 | Carrison et al. ............ 606/200 |
| 2001/0044629 | A1 | 11/2001 | Stinson |
| 2002/0026202 | A1 | 2/2002 | Honey et al. |
| 2002/0045863 | A1 | 4/2002 | Wechler |
| 2002/0107526 | A1 | 8/2002 | Greenberg et al. |
| 2002/0133170 | A1 | 9/2002 | Tsuruta |
| 2003/0171739 | A1 | 9/2003 | Murphy et al. |
| 2003/0195492 | A1 | 10/2003 | Gobron et al. |
| 2003/0225419 | A1 | 12/2003 | Lippitt et al. |
| 2003/0233099 | A1 | 12/2003 | Danaek et al. |
| 2004/0230287 | A1 | 11/2004 | Hartley et al. |
| 2005/0004595 | A1 | 1/2005 | Boyle et al. |
| 2005/0038495 | A1 | 2/2005 | Greenan |
| 2005/0085846 | A1 | 4/2005 | Carrison et al. |
| 2006/0030865 | A1 | 2/2006 | Balg |
| 2006/0052797 | A1 | 3/2006 | Kanamaru |
| 2006/0064113 | A1 | 3/2006 | Nakao |
| 2006/0106417 | A1 | 5/2006 | Tessmer et al. |

OTHER PUBLICATIONS

Written Opinion Issued on PCT/US07/006890, Oct. 4, 2007.

* cited by examiner

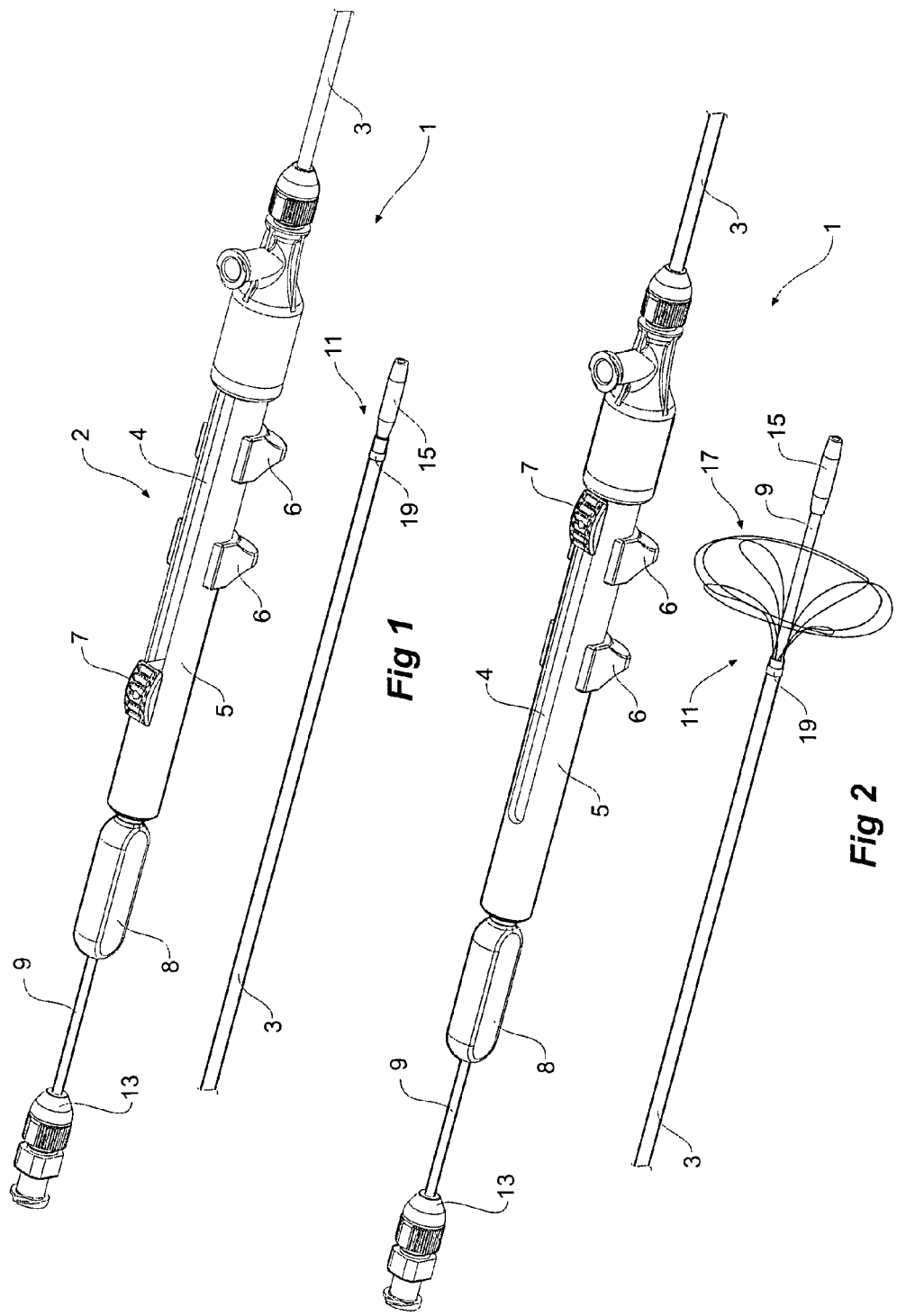

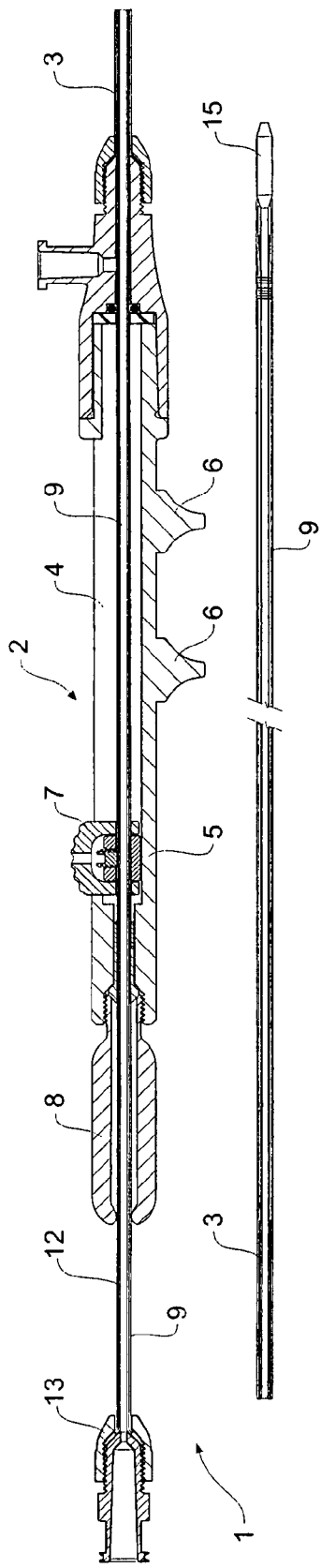
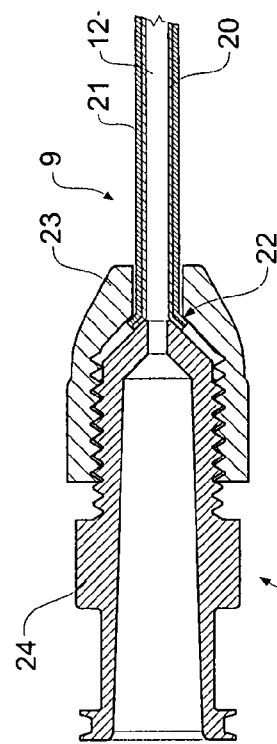
Fig 3
Fig 3A

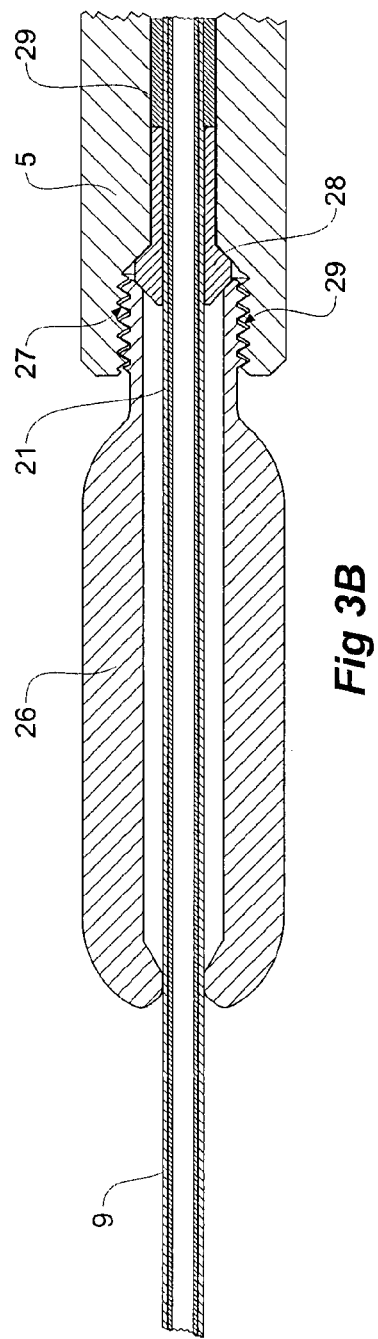
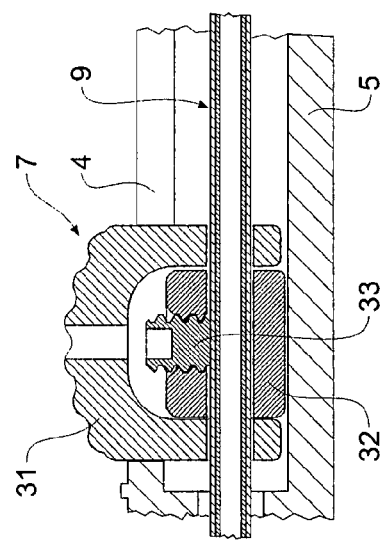
Fig 3B
Fig 3C

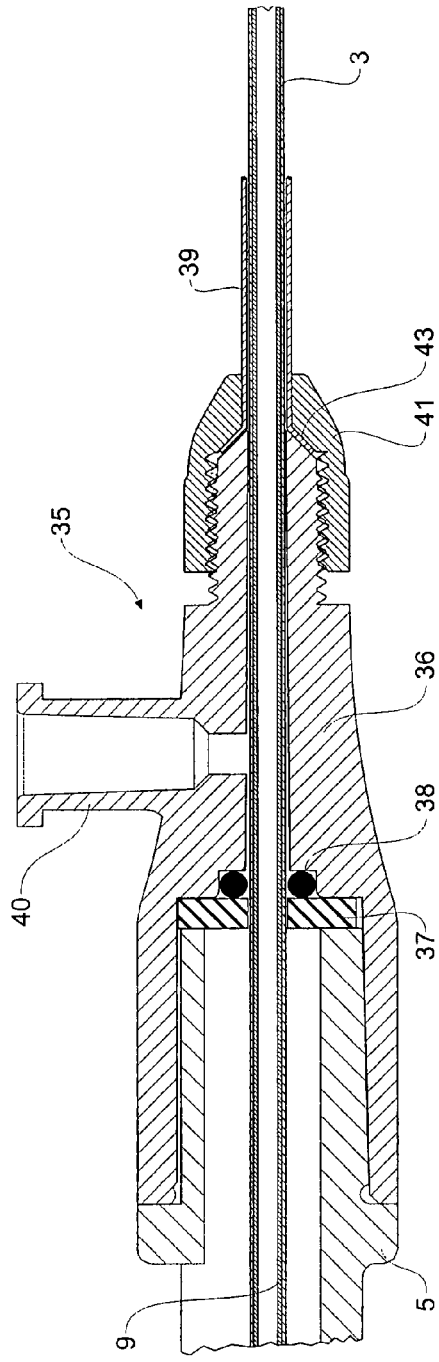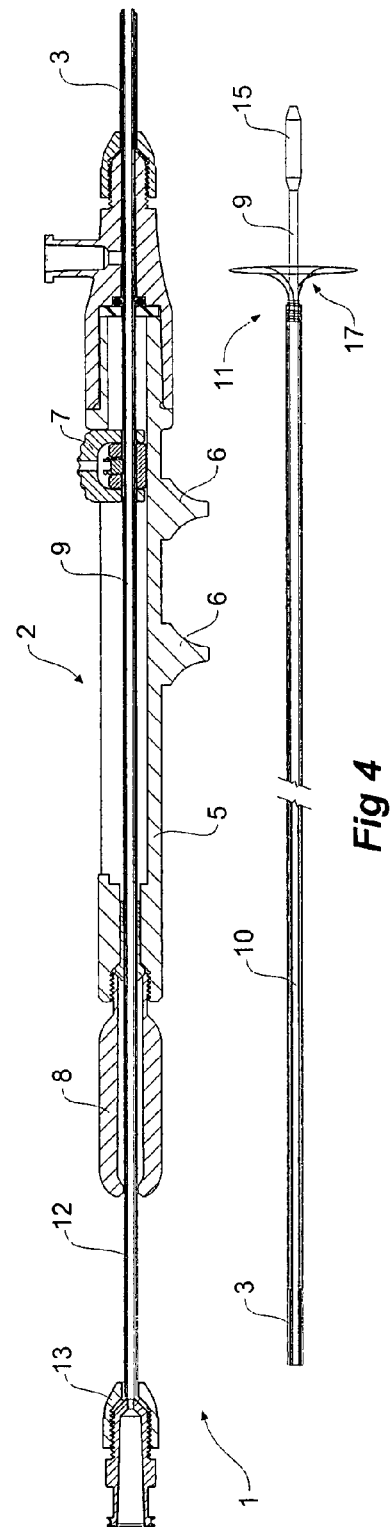

MEDICAL GRASPING DEVICE

CROSS-REFERENCE TO RELATED APPLICATIONS

This application claims priority to my earlier filed Provisional Application, Ser. No. 60/784,126, filed Mar. 20, 2006 and which application is a continuation-in-part of the pending application Ser. No. 10/828,094 filed on Apr. 20, 2004; and a continuation-in-part of application Ser. No. 10/814,018 filed on Mar. 31, 2004; and a continuation-in-part of application Ser. No. 10/814,989 filed on Mar. 31, 2004; and a continuation-in-part of application Ser. No. 10/003,011, filed Nov. 1, 2001, which claims priority to Provisional Patent Application Ser. No. 60/245,811 filed Nov. 3, 2000.

TECHNICAL FIELD

This invention is related to medical devices and in particular to a medical grasping device.

BACKGROUND OF THE INVENTION

There is a current trend in medicine to minimize surgical and interventional procedures, concomitant with the development of minimally invasive tools to access, visualize, infuse, treat, medicate, sample, and interact with internal structures of the body. Occasionally, devices such as catheters, balloons or wires are inadvertently severed in a blood vessel, cavity or organ. Depending on its location, the severed device or fragment must be retrieved. Frequently, a surgical approach is dangerous and costly. In many cases, access has already been established to the severed device, fragment, or foreign body in question, and it is just a matter of locating and removing the foreign body without doing harm to surrounding tissue or forcing it further out of reach.

Certain medical devices are known that are utilized in the ducts and vessels of a human or veterinary patient for retrieval of bodies from the patient. For example, retrieval devices are known for removing calculi such as kidney stones or gallstones from a patient, where the retrieval device is delivered to the target site via the urethra or biliary duct, respectively. The device's distal tip is adapted to deploy at the site to form a basket shape to trap the calculi after which the basket is collapsed to grasp the calculi. Both the device and the grasped calculi are then withdrawn from the patient.

One such stone retrieval device is disclosed in U.S. Pat. No. 5,989,266, in which several loops of wire are caused to emerge from the distal end of a sheath that has previously been delivered through the renal or biliary system of a patient to the site of the stone. The stone becomes trapped within the loops, after which the loops are pulled proximally mostly into the sheath, grasping the stone firmly, after which the sheath, loops and stone are withdrawn from the patient. The loops are disclosed to be made from a superelastic alloy such as Nitinol to automatically form the loops when caused to emerge from the sheath's distal tip. Other similar stone retrieval devices are disclosed in U.S. Pat. Nos. 5,057,114; 5,064,428; 5,133,733 and 5,484,384.

However, use of such devices is not satisfactory for grasping such an object within the vascular system of a patient for repositioning of that object, or for removal of objects from within the vascular system of a patient. For example, in certain situations it is desired to reposition a stent or stent graft within the vasculature, or to retrieve or reposition a malpositioned or misplaced embolization coil. And during delivery and deployment of a bifurcated stent graft at the site of an abdominal aortic aneurysm when surgical access has been obtained through the femoral arteries on both sides of the groin, it is desirable to grasp the distal tip of a guide wire extending into the aneurysm from the contralateral iliac artery, to be pulled into the ipsilateral iliac artery at the vessel's aorto-iliac bifurcation, for eventual placement of the contralateral leg extension of the stent graft.

For vascular use, another known device is a suture loop on a catheter distal tip. Yet another is a guide wire that has been doubled over and extended through a catheter so that its distal end forms into a loop that extends axially from the catheter's distal end to be utilized as a retriever when it is pulled proximally to capture an object and hold it against the catheter distal end for withdrawal, sold as the Curry Intravascular Retriever Set by Cook, Incorporated, Bloomington, Ind. A version of the stone basket device, having helical loops, has been utilized for intravascular retrieval, the Dotter Intravascular Retriever Set also sold by Cook, Incorporated.

In U.S. Pat. No. 5,171,233 is disclosed a snare-type probe for intravascular use. After a catheter is inserted into the patient's vascular system to the site of the foreign object, an elongate member having a loop-shaped distal segment is inserted into the proximal end of the catheter's lumen until the loop-shaped distal segment emerges from the catheter's distal tip at the site. Then the loop-shaped segment extends at an angle to the adjacent portion of the member and opens into a loop. Once a free end of the foreign object is snared within the loop-shaped distal segment as determined by fluoroscopic equipment, the loop-shaped distal segment is pulled proximally into the catheter distal end, collapsing about the ensnared foreign body fragment and holding the foreign body at the distal tip of the catheter during withdrawal. The elongate member is preferably disposed within an outer sheath and is disclosed to be one wire, or two gripped-together wires, of a shape memory material such as a superelastic Nitinol alloy, with a single preformed loop shape at the distal segment defined by two wire portions. The use of Nitinol enables the wire segments defining the distal segment to be straightened and collapsed upon one another into an elastically deformed configuration to pass through the lumen of the catheter and yet automatically open into a loop and extend at a substantial angle upon emerging from the catheter distal tip. One characteristic of this design is that during retraction after grasping, the loop quickly changes, or 'flips' between the angled orientation and a generally axial one, and this results in less assured control over the item during grasping, and commonly will result in escape of the item thus requiring redeployment of the loop for another grasping attempt.

It is desired to provide a medical grasping device for grasping and repositioning an object within the vascular system of a patient, such as a stent or stent graft or embolization coil or such as the distal tip of a catheter or a guide wire; or to grasp a stent or embolization coil, or a fragment from a catheter or guide wire or a pacemaker lead, for its removal from the patient.

It is also desired to provide a low profile, medical grasping device that is conformable to the vascular anatomy while generating a substantial tensile force.

It is further desired to provide such a device that is trackable through the vascular system over a guide wire already in situ. It is yet further desired to provide such a device that is atraumatic to the patient.

Throughout this specification the term distal with respect to a portion of the medical grasping device means the end of the medical grasping device further away from the user and the term proximal means the portion of the medical grasping device closer to the user.

SUMMARY OF THE INVENTION

The foregoing problems are solved and a technical advance is achieved in an illustrative embodiment of a medical grasping device of the present invention. The medical grasping device comprises an elongate control member having a distal tip and a proximal end portion, said elongate control member further including a grasping member proximal said distal tip, an outer sheath with a passageway therethrough surrounding said elongate control member and relatively movable with respect thereto and a control assembly disposed at a proximal end of said outer sheath and said proximal end portion of said elongate control member and in operative relation thereto for urging said grasping member from a distal end of said outer sheath and retraction thereinto, said grasping member comprising a plurality of pre-formed wire loops which self-deploy transversely upon emerging from said distal end of said outer sheath, respective ends of each wire loop being fastened to substantially opposite sides of the elongate control member whereby each of said wire loops is substantially semi-circular upon full deployment and the respective ends of each wire loop extend substantially in opposite directions from the elongate control member.

Preferably each of said wire loops includes side sections that overlap substantially completely with side sections of adjacent ones of said wire loops on each side thereof.

Preferably said elongate control member is a flexible cannula defining a lumen extending therethrough into which a guide wire is receivable and movable with respect thereto.

Preferably said outer sheath is flexible and kink-resistant and has lubricious outer and inner surfaces.

Preferably said control assembly includes an actuation section that is easily able to be gripped for reciprocal movement along a handle to actuate said elongate control member with respect to said outer sheath to deploy and retract said grasping member, respectively.

Preferably said actuation section includes a connecting block affixed to said elongate control member and is disposed within a longitudinal slot in said handle and is movable along said slot between opposite ends thereof. The control assembly can further include a pin vice assembly at the proximal end thereof, the pin vice assembly acting between the control member and the control assembly to prevent relative movement therebetween when engaged.

Preferably the control member comprises an outer rigid tube and an inner flexible tube, the rigid tube extending through the control assembly and into the outer sheath and moveable therethrough. The connecting block can be affixed to the outer rigid tube.

Preferably each of said wire loops includes an arcuate outer section having a radius about equal to a radius of a deployment site of a vessel into which the grasping device is inserted.

Preferably said grasping member comprises four preformed wire loops that self-deploy transversely upon emerging from said distal end of said outer sheath approximately equally spaced angularly about a longitudinal axis of said elongate control member and thereby generally occupy a full cross-section of a vessel into which the grasping device is inserted.

Preferably said grasping member comprises a plurality of wire loops that each are formed from a superelastic alloy.

Preferably said grasping member comprises a plurality of wire loops having proximal end portions that are joined to said elongate control member at affixation joints and initially extend axially from said elongate control member even when said wire loops emerge from said distal end of said outer sheath and self-deploy transversely of a longitudinal axis of the grasping device. The affixation joints can comprise a spiral of the wire of the wire loops around the elongate control member.

Preferably each of said wire loops includes arcuate side sections that upon deployment extends toward a wall of a vessel into which the grasping device is inserted.

Preferably said wire loops comprise Nitinol wire segments.

Preferably the distal tip comprises an atraumatic section.

Preferably the elongate control member is formed for low elongation.

Preferably each of said wire loops includes an arcuate outer section which comprises or includes a radiopaque material. The radiopaque material can comprise a coil of platinum wire around and extending along the arcuate outer section.

The device can include a port fitting to allow flushing with sterile saline solution between the elongate control member and the outer sheath to eliminate air, while the device is outside of the patient. An air seal can be utilized near the distal end of the sheath.

In a second form the invention comprises a medical grasping device comprising an elongate control member having an atraumatic distal tip section and a proximal end portion, said elongate control member further including a grasping member proximal said distal tip section, said elongate control member being formed for low elongation; an outer sheath with a passageway therethrough surrounding said elongate control member and relatively movable with respect thereto; and a control assembly disposed at a proximal end of said outer sheath and said proximal end portion of said elongate control member and in operative relation thereto for urging said grasping member from a distal end of said outer sheath and retraction thereinto, said grasping member comprising a plurality of pre-formed wire loops which self-deploy transversely upon emerging from said distal end of said outer sheath, respective ends of each wire loop being fastened to substantially opposite sides of the elongate control member whereby each of said wire loops is substantially semi-circular upon full deployment and the respective ends of each wire loop extend substantially in opposite directions from the elongate control member wherein each of said wire loops includes side sections that overlap substantially completely with side sections of adjacent ones of said wire loops on each side thereof, said elongate control member is a flexible cannula defining a lumen extending therethrough into which a guide wire is receivable and movable with respect thereto, said outer sheath is flexible and kink-resistant and has lubricious outer and inner surfaces, said control assembly includes an actuation section that is easily able to be gripped for reciprocal movement along a handle to actuate said elongate control member with respect to said outer sheath to deploy and retract said grasping member, respectively and said actuation section includes a connecting block affixed to said elongate control member and is disposed within a longitudinal slot of said handle and is movable along said slot between opposite ends thereof and said connecting block comprises a rigid tube through which extends the elongate control member and the rigid tube extending into the outer sheath and moveable therethrough, the grasping member comprises four preformed wire loops from a superelastic alloy that self-deploy transversely upon emerging from said distal end of said outer sheath approximately equally spaced angularly about a longitudinal axis of said elongate control member and thereby generally occupy a full cross-section of a vessel into which the grasping device is inserted, the wire loops having proximal end portions that are joined to said elongate control member at affixation joints and the affixation joints comprise a spiral of the wire of the wire loops around the elongate control member.

In additional aspects, the grasping device includes a proximal control assembly that is easily manipulated for actuation during grasping, and for assured continued automatic grasping of the object with a controlled, limited amount of force while the device is being moved to manually reposition the object or to remove it completely. The elongate control member is formed to have torqueability and significant tensile strength with low elongation. The outer sheath has a flexible but kink-resistant construction with lubricious outer and inner surfaces.

BRIEF DESCRIPTION OF THE DRAWING

Embodiments of the present invention will now be disclosed by way of example with reference to the accompanying drawings, in which:

FIG. 1 shows a first embodiment of medical grasper according to the present invention;

FIG. 2 the operation of the medical grasper shown in FIG. 1;

FIG. 3 shows a longitudinal cross sectional view of the medical grasper shown in FIG. 1;

FIGS. 3A to 3D show cross sectional details of various portions of the device shown in FIG. 3;

FIG. 4 shows a longitudinal cross sectional view of the medical grasper shown in FIG. 2;

DETAILED DESCRIPTION

Figure 5A:
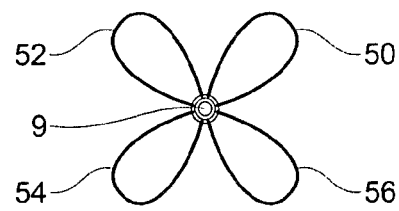
FIGS. 5A to 5C shows various stages of the deployment of the grasping members in end view.

Now looking more closely at the drawings and first in relation to the embodiment shown in FIGS. 1 to 4, it will be seen that the medical grasper 1 includes a control assembly 2 and a sheath 3 extending from the control assembly. The control assembly 2 comprises a fixed handle 5 and a sliding handle 7. The control assembly 2 includes gripper protrusions 6 on the fixed handle 5 to enable a physician to positively grip the fixed handle.

A control member 9 which can be particularly seen in FIGS. 3 and 4 extends from a distal end 11 of the medical grasping device 1 through the sheath 3 and is affixed to the sliding handle 7 in the control assembly 2. The control member 9 then extends further through the control assembly 2 via a locking pin vice 8 to a Luer lock connector 13 at the proximal end of the medical grasping device. The pin vice enables the control member to be locked in a set position. This is particularly useful during advancement and retraction of the medical grasper through the vasculature.

The distal end of the control member 9 in this embodiment terminates in an atraumatic tip 15. The control member 9 comprises a cannula 10 with a longitudinal lumen 12 therethrough through which a guide wire can be passed. The medical grasping device of the present invention can be deployed over a guide wire by extending the guide wire through the lumen 12 of the control member 9. At the distal end of the sheath 3 and there is a radiopaque marker 19 on the control member 9 just proximal of the atraumatic tip 15. The atraumatic tip may be formed from soft nylon or radiopaque urethane material.

As can be seen in FIGS. 2 and 4, the sliding handle 7 has been moved towards the distal end of the control assembly 2 along elongate slot 4 in the fixed handle 5 and this has extended the control member 9 distally to expose a grasping member 17. In FIG. 1 the grasping member is trapped between the sheath 3 and the control member 9 but when the control member is extended distally, the grasping member 17 can expand out. The grasping member comprises a plurality of wires of a shape memory material, which are formed into the extended shape as shown in FIG. 2 and then withdrawn into the sheath as shown in FIG. 1 for deployment. More detail of the grasping member is shown in FIGS. 5 to 8.

The medical grasping device of the present invention is used to grasp objects and particularly guide wires or the like within a lumen of the human or animal body. The medical grasping device is deployed over a guide wire into a lumen of the body in the form shown in FIG. 1 and then the grasping member 17 is extended as shown in FIG. 2. The article such as a guide wire to be grasped is then deployed so that the guide wire for instance extends through the loops of the grasping member and then the sliding handle 7 is retracted to retract the grasping member loops into the sheath until the guide wire for instance has been trapped by the loops and grasped by the engagement of the sheath 3 with the loops of the grasping member 17, and then the guide wire for instance can be withdrawn from the lumen by withdrawal of the whole device while keeping tension on the sliding handle 7 to prevent release of the guide wire 19. Advantageously the pin vice 8 is tightened before retraction to assist with maintaining grip on the grasped object.

The control member 9 is a composite construction consisting of a flexible tube surrounded by a more rigid tube as shown in detail in FIG. 3A. At its proximal end the more rigid tube of the control member 9 extends from the Luer lock connector 13 at the proximal end of the medical grasping device through the control assembly 2 and partially into the sheath 3. The flexible tube can be constructed from a 4.1 French braided nylon catheter and the more rigid tube can be a stainless steel catheter. Both catheters are flared at their proximal ends and clamped into the Luer lock connector 13. The sliding handle or knob clamps onto the more rigid tube as shown in detail in FIG. 3C.

FIGS. 3A to 3D show detail of various portions of the medical grasper and particularly parts of the control assembly.

FIG. 3A shows the Luer lock connector 13 and its connection with the control member 9. The control member 9 comprises a flexible tube 20 surrounded by a more rigid tube 21. The flexible tube 20 has the longitudinal lumen 12 therethrough through which a guide wire can be passed. At their proximal ends 22 they are both flared and clamped between a nut 23 and a Luer lock connector body 24.

FIG. 3B shows the pin vice assembly 8. The pin vice assembly comprises a knob 26 with a screw thread 27 which engages with a screw thread 29 in the rear of the fixed handle 5 and by rotation of the knob 26 causes the knob to engage against a clamp member 28 and this in turn causes the clamp member to clamp against the outer rigid tube 21 of the control member 9. This prevents movement of the control member with respect to the fixed handle 5.

FIG. 3C shows detail of the sliding handle 7 and its connection with the control member 9. The sliding handle 7 has a gripping knob 31 which engages around a clamping block 32. The clamping block 32 has a set screw 33 which engages against the outer rigid tube 21 of the control member 9. Movement of the sliding handle 7 along the slot 4 in the fixed handle 5 will cause the control member to move also provided the pin vice 8 has been disengaged.

FIG. 3D shows a hemostatic seal arrangement between the control member 9 and the fixed handle 5 and the connection of the sheath 3 with the fixed handle 5. The distal end 35 of the fixed handle 5 comprises an adaptor 36 with a combination of a silicone washer seal 37 and an O-ring seal 38 engaged between the adaptor 36 and fixed handle 5. This provides a hemostatic seal for the lumen 39 between the sheath 3 and the control member 9. A flushing port 40 enables supply of flushing fluid into the lumen 39 between the sheath 3 and the control member 9 to allow for instance flushing with sterile saline solution between the elongate control member and the outer sheath to eliminate air, while the device is outside of the patient. The sheath 3 is clamped onto the adaptor 36 by a clamping nut 41 which engages against a flare 43 at the proximal end of the sheath 3.

FIGS. 5A to 5C and 6A to 6C show various stages of the deployment of the grasping member 17 from the end of the sheath 3. The grasping member 17 comprises a number of loops of a shape memory wire such as Nitinol™ wire which are fastened to the control member 9. One method of fastening the wires to the control member is discussed in FIG. 8 below. In this embodiment there are four loops of wire 50, 52, 54 and 56 extending from the control member 9. Each wire loop extends substantially radially outwards from the control member in a first portion 58 and then substantially circumferentially in an arcuate portion 59 before extending radially inwards a portion 60 to the approximate diametrically opposite part of the control member 9 as can be best seen in FIG. 5C. By this arrangement each loop 50, 52, 54 and 56 covers approximately an area of half of a circle and each wire loop overlaps its neighbour on either side by approximately one quarter of a total circle area.

Figure 6A:
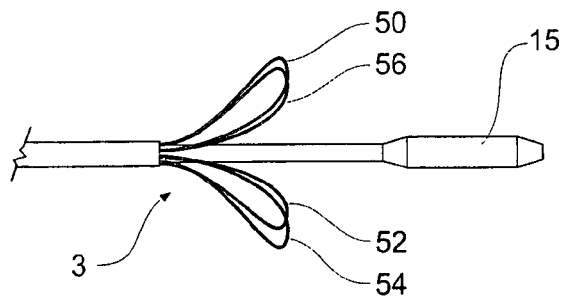
FIGS. 6A to 6C shows various stages of the deployment of the grasping members in side view.

FIGS. 5A and 6A show an initial stage of deployment where the loops of wire 50, 52, 54 and 56 are only just starting to emerge from the sheath from where they are nestled behind the atraumatic tip 15.

Figure 5B:
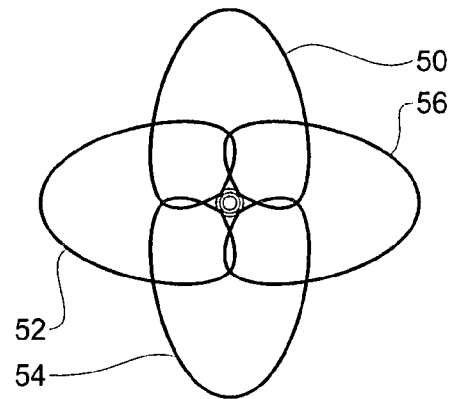
Figure 6B:
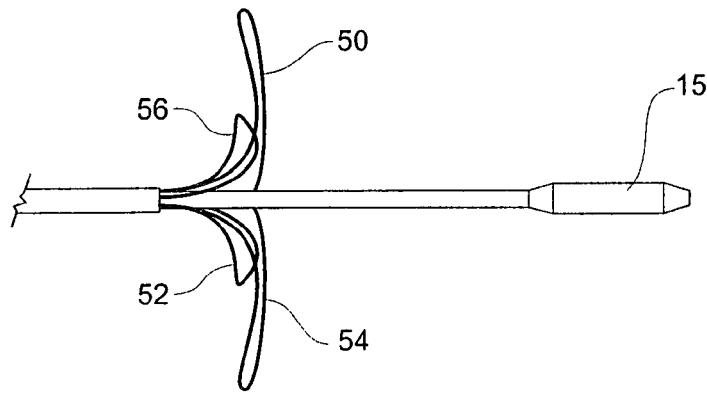

FIGS. 5B and 6B show a further stage of deployment where the loops of wire 50, 52, 54 and 56 are spreading under the influence of their shape memory and are beginning to overlap.

Figure 5C:
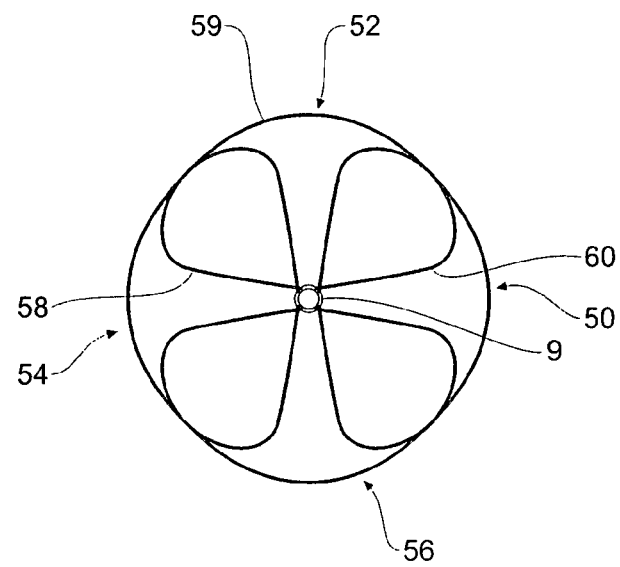
Figure 6C:
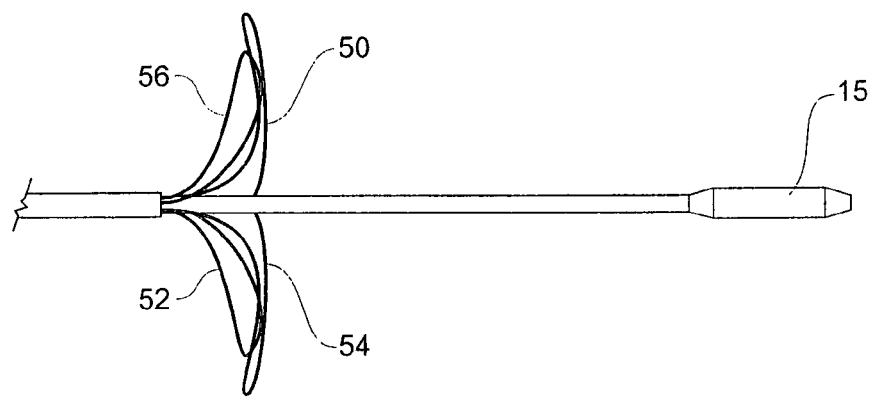

FIGS. 5C and 6C show the final stage of deployment where the loops of wire 50, 52, 54 and 56 are fully deployed and each wire loop overlaps its neighbours on either side by approximately one quarter of a total circle area.

Figure 7:
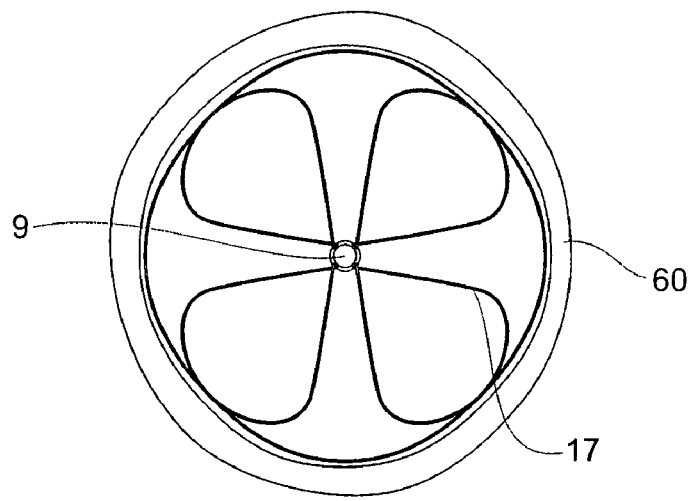
FIG. 7 shows a schematic view of the grasping member expanded into a vessel.

By this arrangement, as shown in FIG. 7 where the grasping member 17 has been deployed into a vessel 60, the wire loops of the grasping member extend right out to the walls of the vessel and completely encircle the walls so any device to be gripped which is passed down through the vessel will be encompassed and conveniently gripped.

It will be realised that the deployed diameter of the grasping member should be selected for the expected diameter of the vessel into which the grasping member is to be used.

Figure 8:
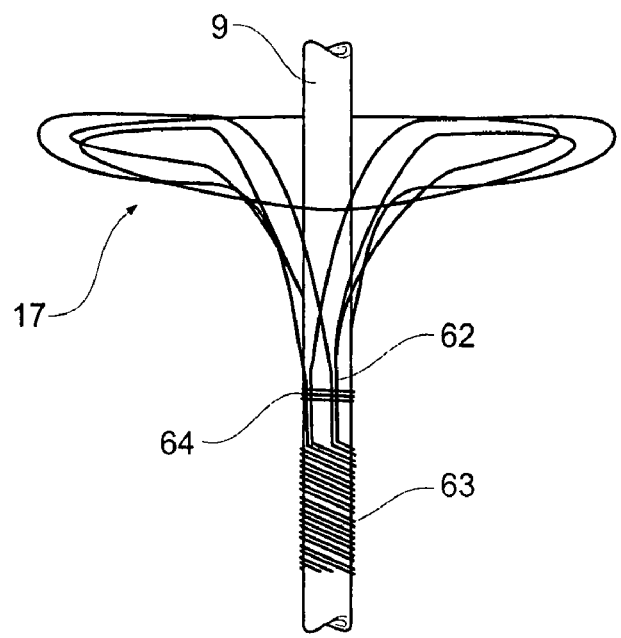
FIG. 8 shows the detail of one embodiment of the grasping member and fastening of the grasping member onto the control member.

One method of affixing the wire loops of the grasping member to the control member according to one embodiment of the present invention is shown in FIG. 8.

As discussed above, the wire loops of the grasping member 17 are formed from a shape memory material such as Nitinol™. Before being placed onto the control member 9, the wire loops are formed on a mandrel with adjacent wires of adjacent loops 62 wound in a series of spirals 63 around a mandrel and then suitably heat treated. After heat treatment, the mandrel is removed and the control member 9 is deployed through the spiral of wire loops so that the spiral of wire loops grips the control member. A binding 64 is placed around the pairs of adjacent wires to keep them adjacent to the control member 9 and a suitable sealing material can be placed over the spiral 63.

Figure 9:
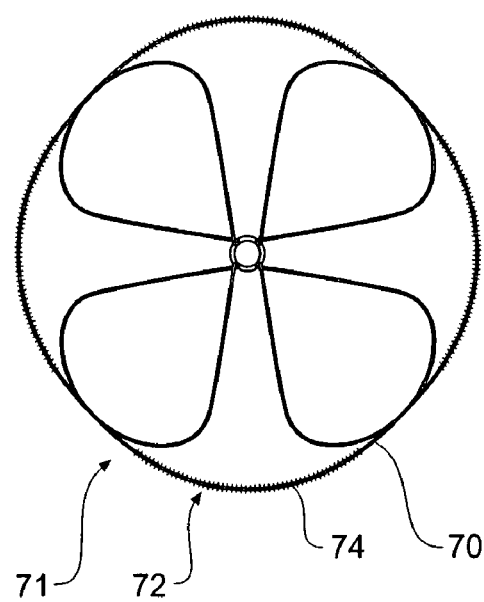
FIG. 9 shows an alternative embodiment of grasping member particularly including radiopaque marking on the wire loops.

FIG. 9 shows an end on view of an alternative embodiment of grasping member 71 according to this invention. In this embodiment, each of the wire loops 70 of the grasping member 71 in its outer region 72 has formed thereon a coil 74 of fine platinum wire to enhance the radiopaque nature of the wire loops.

Figure 10:
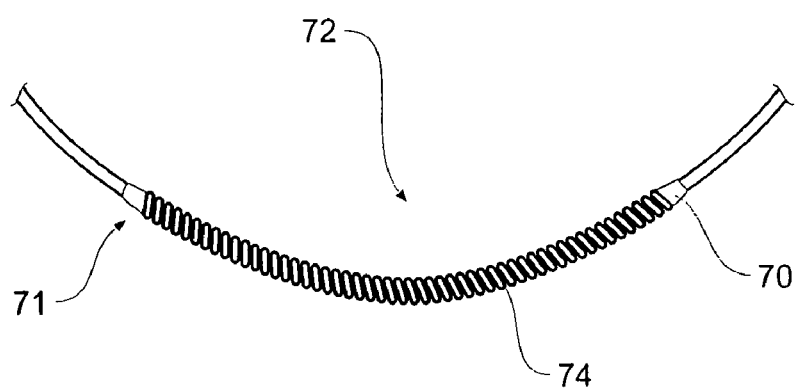
FIG. 10 show a detail of the radiopaque marking onto a wire loop.

FIG. 10 shows a detail of the wire loops with the platinum wire coil 74 formed thereon. At each end of the coil 74, a portion of non toxic adhesive 76 is provided to provide a tapered transition from the coil 74 to the wire 72.

The medical grasping device of the present invention can be useful in any multiple access vascular procedure for adjusting the final position of a medical device, such as through the iliac or subclavian arteries. The invention can additionally be useful with the liver or kidney or other nonvascular procedure, especially where access to the site involves a tortuous path, since the grasping device is flexible and is adapted to follow a guide wire.

What is claimed is:

1. A medical grasping device comprising:
   an elongate control member having a distal tip and a proximal end portion, said elongate control member further including a grasping member proximal said distal tip, an outer sheath with a passageway therethrough surrounding said elongate control member and relatively movable with respect thereto; and a control assembly disposed at a proximal end of said outer sheath and said proximal end portion of said elongate control member and in operative relation thereto for urging said grasping member from a distal end of said outer sheath and retraction thereinto, said grasping member comprising a plurality of pre-formed wire loops which self-deploy transversely upon emerging from said distal end of said outer sheath, respective ends of each wire loop being fastened to substantially opposite sides of the elongate control member whereby each of said wire loops is substantially semi-circular upon full deployment and the respective ends of each wire loop extend substantially in opposite directions from the elongate control member.

2. The grasping device of claim 1, wherein each of said wire loops includes side sections that overlap substantially completely with side sections of adjacent ones of said wire loops on each side thereof.

3. The grasping device of claim 1, wherein said elongate control member is a flexible cannula defining a lumen extending therethrough into which a guide wire is receivable and movable with respect thereto.

4. The grasping device of claim 1, wherein said outer sheath is flexible and kink-resistant and has lubricious outer and inner surfaces.

5. The grasping device of claim 1, wherein said control assembly includes an actuation section that is easily gripped for reciprocal movement along a handle to actuate said elongate control member with respect to said outer sheath to deploy and retract said grasping member, respectively.

6. The grasping device of claim 5, wherein said actuation section includes a connecting block affixed to said elongate control member and is disposed within a longitudinal slot of said handle and is movable along said slot between opposite ends thereof.

7. The grasping device of claim 1, wherein said control member comprises an outer rigid tube and an inner flexible tube, the rigid tube extending through the control assembly and into the outer sheath and moveable therethrough.

8. The grasping device of claim 1, wherein the control assembly further includes a pin vice assembly at the proximal end thereof, the pin vice assembly acting between the control member and the control assembly to prevent relative movement therebetween when engaged.

9. The grasping device of claim 1, wherein each of said wire loops includes an arcuate outer section having a radius about equal to a radius of a deployment site of a vessel into which the grasping device is inserted.

10. The grasping device of claim 1, wherein said grasping member comprises four preformed wire loops that self-deploy transversely upon emerging from said distal end of said outer sheath approximately equally spaced angularly about a longitudinal axis of said elongate control member and thereby generally occupy a full cross-section of a vessel into which the grasping device is inserted.

11. The grasping device of claim 1, wherein said grasping member comprises a plurality of wire loops that each are formed from a shape memory metal or superelastic alloy.

12. The grasping device of claim 1, wherein said grasping member comprises a plurality of wire loops having proximal end portions that are joined to said elongate control member at affixation joints and initially extend axially from said elongate control member even when said wire loops emerge from said distal end of said outer sheath and self-deploy transversely of a longitudinal axis of the grasping device.

13. The grasping device of claim 12, wherein the affixation joints comprise a spiral of the wire of the wire loops around the elongate control member.

14. The grasping device of claim 1, wherein each of said wire loops includes arcuate side sections that upon deployment extends toward a wall of a vessel into which the grasping device is inserted.

15. The grasping device of claim 1, wherein said wire loops comprise Nitinol wire segments.

16. The grasping device of claim 1, wherein said distal tip comprises an atraumatic section.

17. The grasping device of claim 1, wherein said elongate control member is formed for low elongation.

18. The grasping device of claim 1, wherein each of said wire loops includes an arcuate outer section which comprises or includes a radiopaque material.

19. The grasping device of claim 18, wherein the radiopaque material comprises a coil of platinum wire around and extending along the arcuate outer section.

20. The grasping device of claim 1, further including a port fitting on the control assembly to allow flushing with sterile saline solution between the elongate control member and the outer sheath to eliminate air, while the device is outside of the patient.

21. The grasping device of claim 20, comprising a hemostatic seal between the control assembly and the control member.

22. A medical grasping device comprising:

an elongate control member having an atraumatic distal tip section and a proximal end portion, said elongate control member further including a grasping member proximal said distal tip section, an outer sheath with a passageway therethrough surrounding said elongate control member and relatively movable with respect thereto; and a control assembly disposed at a proximal end of said outer sheath and said proximal end portion of said elongate control member and in operative relation thereto for urging said grasping member from a distal end of said outer sheath and retraction thereinto, said grasping member comprising a plurality of pre-formed wire loops which self-deploy transversely upon emerging from said distal end of said outer sheath, respective ends of each wire loop being fastened to substantially opposite sides of the elongate control member whereby each of said wire loops is substantially semi-circular upon full deployment and the respective ends of each wire loop extend substantially in opposite directions from the elongate control member wherein each of said wire loops includes side sections that overlap substantially completely with side sections of adjacent ones of said wire loops on each side thereof, said elongate control member is a flexible cannula defining a lumen extending therethrough into which a guide wire is receivable and movable with respect thereto, said control assembly including an actuation section that is easily gripped for reciprocal movement along a handle to actuate said elongate control member with respect to said outer sheath to deploy and retract said grasping member, respectively and said actuation section includes a connecting block affixed to said elongate control member and is disposed within a longitudinal slot of said handle and is movable along said slot between opposite ends thereof and said connecting block comprises a rigid tube through which extends the elongate control member and the rigid tube extending into the outer sheath and moveable therethrough, the grasping member comprises four preformed wire loops from a superelastic alloy that self-deploy transversely upon emerging from said distal end of said outer sheath approximately equally spaced angularly about a longitudinal axis of said elongate control member and thereby generally occupy a full cross-section of a vessel into which the grasping device is inserted, the wire loops having proximal end portions that are joined to said elongate control member at affixation joints and the affixation joints comprise a spiral of the wire of the wire loops around the elongate control member.

* * * * *